United States Patent [19]

Nielsen

[11] Patent Number: 5,090,420
[45] Date of Patent: Feb. 25, 1992

[54] BLOOD SAMPLING EQUIPMENT WITH NEEDLE HOLDER AND VACUUM VIAL

[76] Inventor: Björn Nielsen, Hvilstedsvej 16, Dk-8355 Solbjerg, Denmark

[21] Appl. No.: 601,709

[22] PCT Filed: Apr. 26, 1989

[86] PCT No.: PCT/DK89/00097
§ 371 Date: Oct. 30, 1990
§ 102(e) Date: Oct. 30, 1990

[87] PCT Pub. No.: WO89/10723
PCT Pub. Date: Nov. 16, 1989

[30] Foreign Application Priority Data

May 2, 1988 [DK] Denmark ............................ 2370/88

[51] Int. Cl.⁵ ................................................ A61B 5/00
[52] U.S. Cl. ..................................... 128/764; 128/766
[58] Field of Search ....................... 128/763, 764, 766; 604/215

[56] References Cited

U.S. PATENT DOCUMENTS

| | | | |
|---|---|---|---|
| 3,469,572 | 9/1969 | Nehring | 128/2 |
| 3,659,587 | 5/1972 | Baldwin | 128/2 F |
| 3,817,240 | 6/1974 | Ayres | 128/2 F |
| 4,166,450 | 9/1979 | Abramson | 128/764 |
| 4,326,541 | 4/1982 | Eckels | 128/766 |
| 4,412,548 | 11/1983 | Hoch | 128/764 |
| 4,416,291 | 11/1983 | Kaufman | 128/766 |
| 4,418,703 | 12/1983 | Hoch et al. | 128/766 |
| 4,436,098 | 3/1984 | Kaufman | 128/766 |
| 4,445,896 | 5/1984 | Gianturco | 604/238 |

Primary Examiner—Max Hindenburg
Attorney, Agent, or Firm—Antonelli, Terry Stout & Kraus

[57] ABSTRACT

Equipment for sampling blood is disclosed which includes an outwardly projecting needle, a vial holder with an internally projected needle and a movable valve means at an end of the needle, and a vacuum vial which slides within the vial holder and is punctured by the internally projected needle while opening the valve means for blood flow from the outwardly projecting needle to the internally projecting needle and into vacuum vial.

3 Claims, 1 Drawing Sheet

BLOOD SAMPLING EQUIPMENT WITH NEEDLE HOLDER AND VACUUM VIAL

BACKGROUND OF THE INVENTION

The present invention relates to an equipment for blood sample collection, i.e. an equipment comprising a hypodermic needle and a needle holder, which also includes a receiver cylinder for an evacuated vial. This vial has a perforatable end cap which at the insertion of the vial into the holder is perforated by an interior needle therein, such that hereby a suction connection is established between the specimen vial and the outer sampling needle. In so doing the collection of blood will be supported by the vacuum in the specimen vial, such that advantageously essentially thinner sampling needles than in the conventional, so-called open systems may be used.

When using such a closed system it is customary that in connection with the said holder a needle is used having a holding piece which can be connected to a stub on the holder and which has a two-sided protruding needle which is pointed at both ends and constitutes both the sampling needle and the associated inner needle in the holder for cooperation with the specimen vial. However, various problems are connected with this simple design, among others that the twin needles concerned are dangerous to handle. They are also problematic in those cases where it is relevant to fill more vials from one and the same insertion of the sampling needle, as in the intermediary periods blood may freely seep from the needle. This, however, is sought counteracted by using a resilient lining tube on the inner needle, this tube in its free state covering an outer, radial outlet opening in the needle, while the tube is axially pressed together for exposure of this opening by insertion of the needle through the end cap of the specimen vial, but the corresponding closing of the opening at the withdrawal of the vial is not fully effective.

DESCRIPTION OF THE PRIOR ART

According to the U.S. Pat. Nos. 4,166,450 and 4,312,362 sampling devices have been contrived where a separation is introduced between the outer, fixed or loose sampling needle and the inwardly projecting needle for connection to the vial, in that an intermediate chamber is provided with transparent walls, which are claimed to provide a visual indication that the sampling needle upon insertion has hit a blood vein such that connecting the vial may wait until it has been ascertained that the sampling will succeed. This may well cut back on certain abortive sampling attempts and a futile use of a number of vials, but in practice this problem is not abundant.

It is more significant that at the same time the environmental problem regarding use of double projecting needles is solved, viz. by the inner needle of the holder constituting a separate portion which both before and after use is situated connected to and protected by the surrounding holder, which does not appear to be recognized previously as a particular advantage on its own.

Comparing the said patent specifications it has been found natural that in the said discontinuous connection between the inner and outer needle, special valve portions may be used instead of the said resilient covering tube over the inner needle. One of the specifications (4,312,362) discloses that a valve slide is brought to uncovering a hole at the side of the inner end of the interior needle in response to the vacuum which is applied by the connection of the vial, but this construction will hereby be limited to a one-off use for filling of a single vial only, as no means are present for resetting the valve slide.

In the other of the said USA Patent specifications, viz. U.S. Pat. No. 4,166,450, an application of an inner needle is proposed, which is limited displaceable in a tight guide in such a manner that at the insertion of the vial into the holder, it is caused to be moved forward to perforating a thin separator diaphram adjacent an antechamber, which is connected to the rear end of the sampling needle, prior to the opposite end of same needle by the insertion of the vial penetrating the thicker end cap of the vial. This necessitates that the thus displaceable needle portion is connected to radially outwardly projecting guiding and end stop portions entailing problems with regard to a free movability in surrounding, non-ventilated guiding chambers.

SUMMARY OF THE INVENTION

The purpose of the invention is to provide a blood specimen collection system of the said kind by which the necessary valve function can be ensured in a suitable, effective and constructively simple manner.

According to the invention this is achieved by the blood specimen device wherein the valve element is hereby constituted by the inner needle itself, which at the insertion of the vial is pushed to an open position in that the closed front of the needle is brought into engagement with the bottom end of the cylinder, such that the needle thereupon at its pointed tailend is able to perforate the seal of the vial by further insertion of the latter. At retraction of the vial the needle will be brought along to the closed position without any displacement problems, whereby the equipment can be reused for insertion of a new vial. For the simplicity of the construction it is of significance that the inner needle and the outer sampling needle or its holding base are placed radially offset from one another, as the inner needle can thereby be opened by being pressed against a stop, which lies offset from the connecting passage to or from the sampling needle; hereby it can be totally avoided that the inner needle must be connected to special, problem incurring guiding and stop portions, cf. U.S. Pat. No. 4,166,450.

It is hereby an extremely lucky or significant circumstance that also for other reasons it is advantageous that the inner and the outer needle are radially offset from one another, viz. by a central positioning of the inner needle and an eccentric or peripheral placing of the outer needle. By the central placing of the inner needle this will cooperate with a central perforation area on the inserted vials, whereby it may suffice for these to have a comparatively narrow perforation area, and by the eccentric positioning of the outer needle it is possible to insert the needle into the patient at a shallow angle relative the actual body surface, which is advantageous for a good insertion safety and a resulting light fixing of the holder to the part of the body. This advantage in itself is clearly disclosed in the said U.S. Pat. No. 4,166,450 where the advantage is achieved only at the cost of considerable problems with regard to the guiding and valve function of the inner needle which is lying co-axially to the outer needle.

If required the holder may be made of a transparent material such that the insertion of the vial may wait until it is ascertained that a trace of effusing blood from the sampling needle appears at the bottom portion of the holder.

The invention, which also comprises a particularly advantageous design of the vials, is explained in further detail in the following with reference to the drawing, in which:

DESCRIPTION OF THE PREFERRED EMBODIMENT

Figure 1:
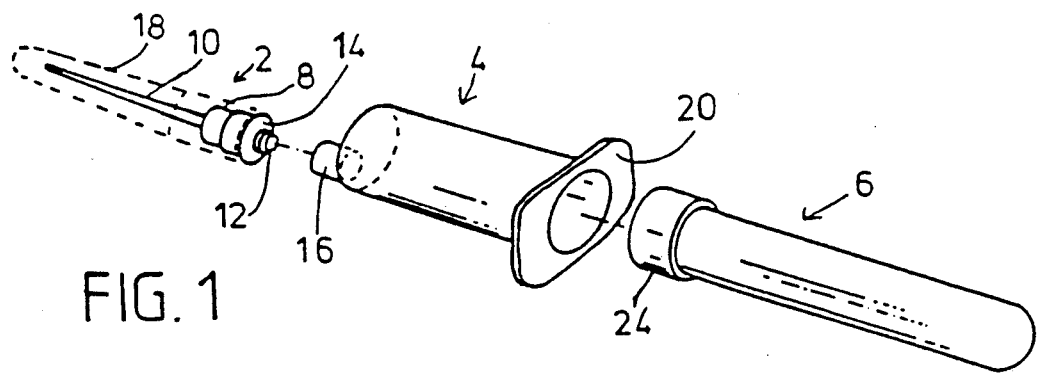
FIG. 1 is an exploded perspective view of a set of collection appliances constituting part of a collection system according to the invention.

In FIG. 1 is shown a collection set comprising a sampling needle 2, a holder 4 and a vial 6. The needle 2 is made in the usual manner for injection needles, viz. comprising a holder portion 8 having a one-sided projecting needle 10 and a bushing 12 at the other side of a collar 14. The bushing 12 is intended for insertion into or screwing onto a connector stub 16 on the holder 4, this being easily performed when a cover 18 is placed over the needle, such cover encasing the needle 10 and being removed after the fitting, when the appliance is required.

The holder 4 is tubular having a closed end at the stub 16 and an opposing open end where the tube comprises a protruding collar 20. Inside the holder 4 and in connection with the stub 16 a central needle 22 is placed projecting slightly inwardly into the holder, however nowhere near to the area at the open end, such that in practice this needle is inaccessible to contact.

The vial 6 is an evacuated glass, the mouth of which is covered by a cap 24 that can be perforated by the needle 22 when the vial is inserted into the holder 4. The perforation requires a certain pressure, but the vial can be pressed in with quite a heavy force, using the collar 20 as a grip just like when pressing home a syringe piston.

The appliances can be applied such that the needle 10 upon assembly with the holder 4 is inserted into a vein whereupon the vial 6 is inserted and is pressed into the holder 4. When the needle 22 penetrates the cap 24, the vacuum in the vial 6 spreads to the foremost needle 10 and the blood is drawn to the vial 6. When this is filled as required it can simply be removed from the holder, which is easily done because the vial in the inserted position protrudes substantially rearwardly from the holder. If no more samples are to be collected, the needle 10 may be withdrawn and provided with the cover 18, after which the unit 2, 4 may be taken to waste collection.

If yet another or some more samples are to be collected, the needle 10 may remain in the vein, and upon removal of the vial 6 a new vial 6 may be inserted into the holder. As mentioned previously it is hereby desirable that use is made of a valve-blocking of the needle 22. In principle this can be brought about in the same way as with the hitherto used rearward protruding needle portions on the needles 2, viz. by covering of the needle 22 with a resilient, narrow case which at the pressing against the cap 24 will become perforated and be pushed forward to exposing the needle, but according to the invention it is preferred to make use of a valve device, which is effective at the fixed end of the needle.

This is rendered possible by virtue of the needle 22 being subjected to a forwardly displacing force by the insertion of the vial 6 already before the cap is perforated, just as the needle, by the frictional engagement with the perforation portion of the cap, will be affected by an outward-directed force, when the vial is removed, and hereby it is possible to lodge the needle thus axially displacable that at the insertion and removal of the vial it will be displaced between two positions in such a manner that the needle in itself hereby can act as a relevant valve member.

Figure 2:
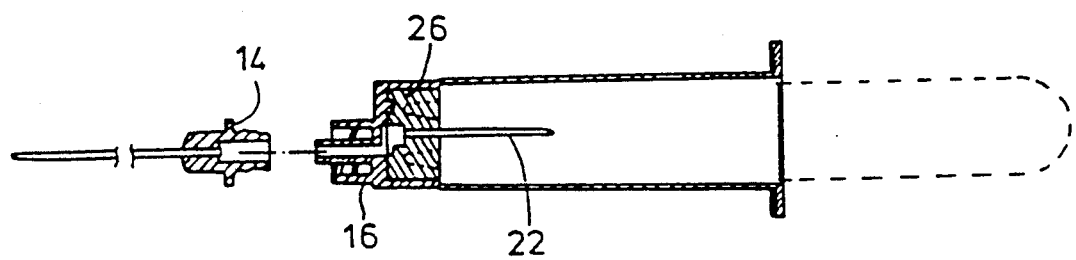
FIG. 2 is a lateral sectional view of two of the appliance components.
Figure 3:
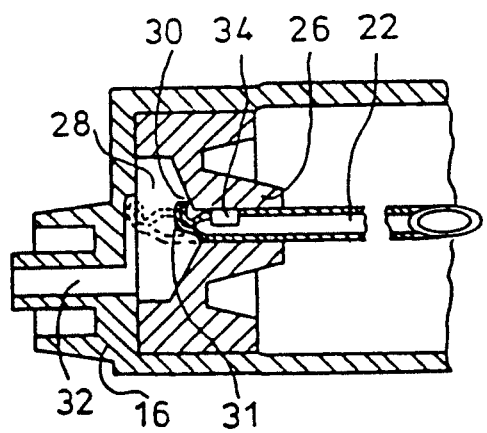
FIG. 3 is a more detailed sectional view of an end portion of the applied holder.

Such an arrangement is shown in further detail in FIG. 2 and particularly in FIG. 3. The needle 22 is mounted in a passage in a holder plug 26, which is pressed in to a position right against the closed end of the holder 4, and outermost this passage communicates with a recess 28 in the plug 26, the needle from the beginning being mounted such that with its rearmost collar portion 30 it abuts on the recess bottom at the relevant end of the said passage for the needle. Close to its outer circumference the recess 30 is in open connection with a central passage 32 through the stub 16 on the holder 4, this stub being placed eccentric on the end portion of the holder, while the needle 22 is situated centrally in the holder. The end of the needle at the collar 30 is closed tightly, preferably by being pressed together and folded out as shown by 31.

The eccentric position of the stub 16 is tantamount to the outer needle 10 being situated close to the extension of an outer wall area of the holder 4, which is an advantage at the insertion of the needle into the vein, as the holder then permits a very acute-angled insertion of the needle into the vein.

The portion of the inner needle 22 which is accommodated in the passage in the plug 22 is provided with side openings 34 which are kept closed by the passage in the position shown by solid lines in FIG. 3. However, at the insertion of the vial 6 the needle will be pushed back when the cap 24 is pressed against its point, and hereby the needle will be displaced to the position shown in dashed lines in which the collar 30 pushes against the front of the holder 4, and in which the side openings 34 communicate with the recess 28 and thereby with the passage 32 through the stub 16, i.e. the needle 22 will thereby communicate with the outer needle 10. Immediately thereafter the point of the needle 22 will penetrate the cap 24 as the needle 22 is now prevented from further displacement, and the vacuum in the vial will thus spread to the collection needle 10.

When the vial 6 is extracted, the needle 22 will be carried along the first stretch as care is taken that its frictional connection with the cap 24 is stronger than its friction with the passage through the plug 26, and the first result of the extraction will thus be that the needle 22 is brought back to the position in which the side openings 34 are situated inside the said passage, i.e. closed outwardly, and as also the free tail end of the needle is closed at 31, the interior of the needle is thus completely blocked from the connection with the recess 28 and the needle 10. The remaining vacuum in the vial 6 will, however, affect the interior of the needle 22 all the time until the cap is moved outwardly past the needle point and there will be an insignificant risk that hereby even a mere trace of a drop of blood will be deposited on the central outside of the cap. At the insertion of a new vial 6 the described course will merely be repeated.

It is essential that the relations are thus adapted that the friction of the needle 22 against the perforated cap 24 is larger than its friction with the passage in the plug 26, and therefore it is also significant that the cover of the vial is adapted according to this condition. The vials used so far for the purpose are provided with a cap consisting of a simple rubber plug with a central depression facilitating the penetration by the needle, but with the prior art it was needless to pay the said special regard to friction, and these plugs were therefore not provided with any especially well calibrated perforation portion. By the invention it is preferred to work with a newly innovated type of vial, where the perforatable element is a disc of rubber or a corresponding material which is clamped by means of a screw cap mounted on a threaded element closely connected with the vial glass, as such an embodiment with increased safety can be adapted to the purpose and besides shows further advantages.

Figure 4:
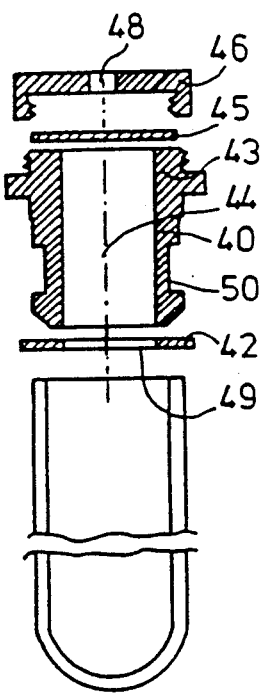
FIGS. 4 and 5 are sectional views of an embodiment of a vial for use in the system.
Figure 5:
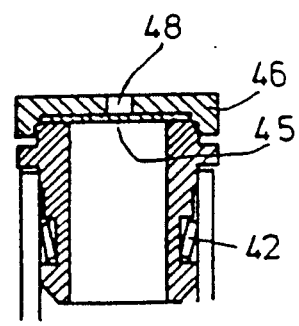

An example of such a vial is shown in FIGS. 4-5 where a plug 40 is inserted in the vial mouth so as to seal against the vial by means of a sealing ring 42, the plug having a protruding portion 43 which is provided with an outer threading. The plug has a completely open central passage 44, and on top of the plug a rubber disc 45 is laid, which is tightened against the plug by means of a screw cap 46 in the overside of which is provided a central hole 48. The unit 40, 45, 46 can be assembled in advance for closing the vial at the evacuation thereof, and at the use the needle 22 needs only to penetrate the disc 45. It is not crucial whether this perforation takes place exactly centrally, but structurally it is convenient letting the needle 22 be centrally placed.

As shown in FIG. 4 the sealing ring 42 is provided as a flat disc having a hole 49, the diameter of which is noticeably smaller than the outer diameter of the plug area 50, on which the ring is to be mounted by insertion from the free end of the plug portion 40. By this insertion the disc 42 will be deformed as shown in FIG. 5, viz. to forming of an upwardly conical expanding tube portion, which by insertion into the vial can tighten firmly against the inside of the latter even though tolerance deviations occur with respect to the inner diameter of the vial and the outer diameter of the sealing disc 42.

At the manufacture of the evacuated vials 6 the assembled plug body can be inserted into the vial while this is kept under vacuum.

When a vial has been filled to a required degree, it is normally desirable immediately upon extraction from the holder 4 to 'deflate' the vial to remove the remaining vacuum therein. This may simply be done by unscrewing the screw cap a little and then screwing it home again; at its edge the sealing disc 45 is secured to the screw cap such that it is compulsorily lifted by the unscrewing.

The blood sample can be taken out after unscrewing the cap 46 either by pouring out or by drawing by a pipette. The plug unit shown has the great advantage that it is thus easily opened without removing the plug, and that the plug, however, is removable from a smooth cylindrical vial which thereby after centrifuging can cooperate with a serum separator. It has previously been attempted to provide the vial glass itself with an outer thread for a screw cap, but this is hardly possible without deformation of the smooth cylindrical inside, and thereby the vial is made unsuitable for cooperation with a usual serum separator.

Figure 6:
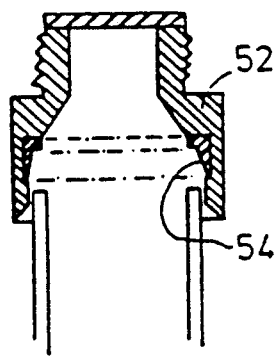
FIG. 6 is a sectional view of another embodiment of the vial.

In FIG. 6 is shown another embodiment of the vial, where the holding plug for the non-illustrated screw cap comprises a bushing portion 52, which can be placed on the outside of the vial mouthing and tightened against the latter by means of an embedded sealing ring 54. This embodiment, which likewise cooperates with a smooth-walled vial, is advantageous by being easily 'deflated' when this is required, as one may press against the lower edge of the portion 52 and thereby produce a capsizing.

I claim:

1. Equipment for sampling blood with a needle, a holder and a vacuum vial for collecting blood, comprising a combined needle and vial holder in the form of a cylinder having an open and a closed end, the closed end accommodating a holding socket for receiving an outwardly projecting sampling needle, an internal needle projecting freely internally in the cylinder from the closed end, the internal needle being adapted to perforate an end closure of an associated evacuated vial when the vial is inserted into the cylinder, the closed cylinder end including a passage capable of connecting the internal needle with the sampling needle through valve means actuated by the insertion of the vial, wherein the valve means comprise the combination of the internal needle being mounted for limited displacement in the holder so as to be displaceable forwardly and rearwardly, respectively, in response to insertion and retraction of the vial, and the internal needle is formed so as to be closed at is foremost end while having adjacent that end a side orifice, which cooperates with a surface of a closing bushing of the holder which surrounds a portion of said needle for opening and closing the side orifice thereof by the relative displacements of the needle with respect to the bushing and holder; the closing bushing is a fixed, central part of the foremost end portion of the holder, and adjacent is closed front end the internal needle is formed with a radial widening portion that blocks the needle against retraction, while a corresponding stop for the forward displacement is formed by a central inner side portion of a foremost end wall of the holder, said foremost end wall being provided with the said holding socket for the sampling needle in an eccentric position relative the end wall.

2. The blood sampling equipment according to claim 1, wherein the guiding and closing bushing for the internal needle is mounted against the inside of the end wall of the cylinder and is shaped with a cylindrical depression that faces this wall with a width sufficient to communicate with an intake passage through the eccentrically disposed holding socket.

3. The blood sampling equipment according to claim 1, wherein the associated vial is provided with a plastic plug having a plug or skirt portion, which cooperates with a smooth walled mouthing portion of the vial glass and accommodates one or more sealing rings, said plastic plug further including a threaded cylindrical portion which projects from the vial glass and holds a screw cap having a central hole in a lid plate portion of the screw cap, a perforatable sealing disc being located between the lid plate portion and the free edge of the threaded cylindrical portion.

* * * * *